United States Patent
Gandhi

(10) Patent No.: US 9,861,281 B2
(45) Date of Patent: Jan. 9, 2018

(54) TELEMETRICS AND ALERT SYSTEM

(71) Applicant: Accenture Global Services Limited, Dublin (IE)

(72) Inventor: Jimit Jaykumar Gandhi, Pune (IN)

(73) Assignee: Accenture Global Services Limited, Dublin (IE)

( * ) Notice: Subject to any disclaimer, the term of this patent is extended or adjusted under 35 U.S.C. 154(b) by 0 days.

(21) Appl. No.: 15/074,405

(22) Filed: Mar. 18, 2016

(65) Prior Publication Data
US 2016/0270659 A1   Sep. 22, 2016

(30) Foreign Application Priority Data
Mar. 19, 2015   (IN) .......................... 1377/CHE/2015

(51) Int. Cl.
*A61B 5/00*    (2006.01)
*G06F 19/00*   (2011.01)
*H04Q 9/00*    (2006.01)
*G06F 19/28*   (2011.01)

(52) U.S. Cl.
CPC .......... *A61B 5/0015* (2013.01); *G06F 19/363* (2013.01); *H04Q 9/00* (2013.01); *G06F 19/28* (2013.01); *H04Q 2209/40* (2013.01); *H04Q 2209/43* (2013.01); *H04Q 2209/823* (2013.01)

(58) Field of Classification Search
CPC ....... A61B 5/0015; A61B 5/16; A61B 5/4082; A61B 5/7275; G06F 19/3418; G06F 19/363
See application file for complete search history.

(56) References Cited

U.S. PATENT DOCUMENTS 7,634,662 B2 * 12/2009 Monroe ............. G06K 9/00221
                                                                    382/117
2015/0265205 A1 * 9/2015 Rosenbek ............ A61B 5/4082
                                                                    600/586

OTHER PUBLICATIONS

Lee, H., Park., S.H., Woo, E.J., "Remote Patient Monitoring Service through World-Wide Web," dated Oct. 30, 1997, pp. 1-4, Proceedings—$19^{th}$ International Conference—IEEE/EMBS, Oct. 30-Nov. 2, 1997, Chicago, IL XP-002129894.

* cited by examiner

*Primary Examiner* — Kabir A Timory
(74) *Attorney, Agent, or Firm* — Brinks Gilson & Lione

(57) ABSTRACT

A telemetric monitoring system and data analysis tool is provided that assists in trial management by identifying relationships between subject profiles and monitors physiological attributes using telemetric devices. The tool may identify subjects having certain response predispositions based on their profiles, which may be used to better select subjects to enroll in a trial. The system may monitor the physiological attributes of a subject to identify adverse events, and may generate event alerts that are sent to investigators over a communication channel. The system may present the investigators with a dashboard through which they can investigate and respond to event alerts.

17 Claims, 8 Drawing Sheets

Figure 5

TELEMETRICS AND ALERT SYSTEM

RELATED APPLICATIONS

The present patent document claims the benefit of priority to Indian Provisional Patent Application Ser. No. 1377/CHE/2015, filed on Mar. 19, 2015, and entitled "PATIENT TELEMETRICS AND ALERT SYSTEM," which is incorporated by reference herein in its entirety.

TECHNICAL FIELD

This disclosure relates to a system and method for use of remote monitoring tools.

BACKGROUND

The discovery and development of new drugs and medical innovations is often times a long (10-15 years) and costly process (1.5-2 billion dollars). Specifically, drugs must undergo a rigorous multi-phase clinical trial process, lasting several years (6-7 years), in which the effects of a drug are studied in volunteer patient populations. For instance, Phase-I trials may involve 20-100 volunteers, Phase-II trials may involve 100-500 volunteers, and Phase-III trials may involve 1000-5000 volunteers. In conducting such trials, trial coordinators often look to see if volunteers match certain sponsor defined criteria, and if so the patient is enrolled in a randomization study.

This screening process, however, is relatively limited, and a significant number of adverse events are nevertheless experienced in clinical trials, with over 3 million adverse drug reactions and 1 million deaths reported annually. The occurrence of adverse events may operate to extend the length of the trial and result in increased costs, and may be responsible, in part, for the high rate of clinical attrition, with a 40-45% failure rate experienced in Phase-III trials—where most of the failures are attributed to lack of sufficient efficacy and safety data. The clinical trial process is further complicated by the need for patient monitoring, which is generally performed during doctor visits to the study or testing site. However, such methods are not well suited for serious adverse events, which may require immediate medical attention.

Accordingly, a need exists for a remote monitoring tool that provides for early and targeted stratification of patients, which may result in improved drug success rates, increased drug response predictability, and improved identification of causal links between drug treatments and adverse events.

SUMMARY

The systems and methods described below may provide a tool for smarter clinical trial management by leveraging modern patient testing and real-time, or near real-time, medical device data. By looking at a personalized profile of a patient (e.g., a genomic profile or metabolomics profile), clinicians may be able to perform patient specific assessments of a drugs suitability and efficacy, for example, allowing physicians to pre-identify patients who are most likely to experience severe side effects from medications, or to predict which patients might require alternative dosing. This patient specific information may also be incorporated into the decision-making process when prescribing medications as a way to individualize therapies. Capturing and analyzing medical device data in real-time may allow clinicians to more readily observe adverse events experienced by a patient, provide for more rapid treatment, and predict future adverse events in similarly situated patients (i.e., patients having similar profiles) so that proactive measures can be taken to avoid a negative outcome. In this way, the system may help to save patient lives, reduce the costs associated with clinical trials, reduce the probability of drug failure, speed up clinical trial process, and aid in new clinical trial designs.

Other embodiments of the systems, methods, features, and their corresponding advantages will be, or will become, apparent to one with skill in the art upon examination of the following figures and detailed description. It is intended that all such additional systems, methods, features, and advantages be included within this description, be within the scope of the invention, and be protected by the following claims.

BRIEF DESCRIPTION OF THE DRAWINGS

The described system for clinical trial management may be better understood with reference to the following drawings and the corresponding description. The components in the figures are not necessarily to scale; instead, emphasis has been placed upon illustrating the principles of the invention. Moreover, in the figures, like reference numerals designate corresponding parts throughout the different views.

FIG. 5 illustrates an example of a second view of a uniform consolidated output provided through an interface that the system may provide to clinical investigators.

DETAILED DESCRIPTION

Through the advance of scientific technology, medical researchers and physicians now have the ability to rapidly and accurately determine millions of pieces of genetic information for individuals who choose to be tested. Clinicians, through statistical and quantitative analysis, may use this information to determine the role that genetic and environmental factors have on health and disease in large groups of patients. Clinicians, for example, may look to assess the association between complex diseases and the genomic profile of a patient. Clinical investigators may look at the association between Single Nucleotide Polymorphisms (SNPs), which indicate variations in a single nucleotide occurring at a specific position in the genome, and a particular disease, drug or drug treatment regimen. Clinical investigators may also look at other genomic data involved in the mechanism from SNPs to disease, to help identify associations between the genomic data and the particular disease, drug or drug treatment (e.g., identify a SNP profile within a particular patient population). While the foregoing description may reference a genomic profile that is based on the presence of certain SNPs, a patient's genomic profile is not thus limited and may be adapted to account for other genomic data (e.g., height or biomarker concentrations, etc.). Moreover, while the genomic profile of a user may provide some indication as to a patient's medical predisposition, the mechanisms by which an individual patient responds to a particular drug treatment are far more complex and may be influenced by additional factors. For example, a patient specific metabolic profile, which looks at the metabolic pathway through which a drug is consumed and quantifies the presence or intensity of a metabolic phenotype (metabotype), may similarly reflect a medical predisposition of a patient. Accordingly, while the foregoing description is primarily made with reference to a genomic profile, the invention is not thus limited, and may take into account other patient specific profiles including, for example and without limitation, transcriptomic, proteomic, metabolomic, and autoantibody profiles of a patient.

Figure 1:
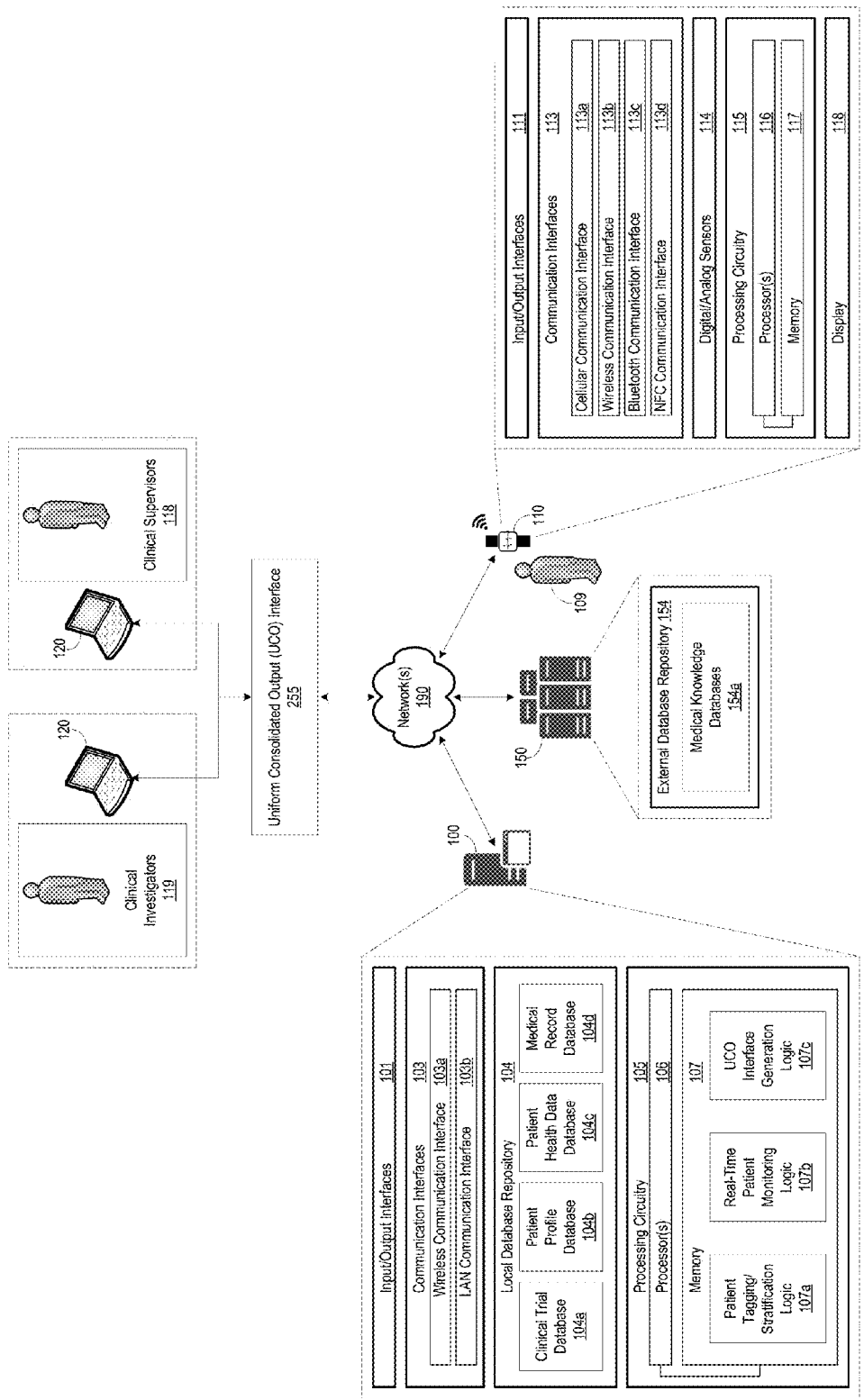
FIG. 1 provides an example of the environment in which one embodiment of the clinical trial management system may operate.

FIG. 1 provides an example of the technical environment 101 in which the clinical trial management system 100 ("system 100") may be deployed. The environment 101 may include the system 100, third party database servers 150, telemetry devices 110 for clinical trial patients 109, and terminals and work stations 120 for clinical supervisors 118 and clinical investigators 119, all of which may communicate with (i.e., transmit data to and receive data from) one another over one or more network(s) 130. The network(s) 130, for example, may include private enterprise networks (e.g., the intranet within a given enterprise) and public networks (e.g., including the Internet), which may utilize any number of networking protocols, now available or later developed, during communication, including but not limited to TCP/IP based networking protocols.

The system 100 may include one or more input/output interfaces 101, one or more communication interfaces 103 (e.g., a wireless communication interface 103a and a LAN communication interface 103b), a local database repository 104, and processing circuitry 105, which may include a processor 106, a memory 107 that includes one or more processors 226 and memory 227. The memory 107 may include patient tagging and stratification logic 107a, real-time patient monitoring logic 107b, and Clinical Trial Management Platform (CTMP) logic 107c. The patient tagging and stratification logic 107a may include logic for analyzing a patient profile (e.g., a genomic profile or metabolic profile) to identify medical predispositions of the patient. The real-time patient monitoring logic 107b may capture, store and process real-time health data received form the telemetry devices 110 of clinical trial patients 109. The CTMP logic 107c may generate an interactive interface through which clinical investigators 119 may interact with the system 100. The CTMP interface provided by the CTMP logic 107c may assist the clinical investigators with registering new clinical trials, managing recruitment of patients to the different clinical trials, monitoring the health of patients enrolled in the different clinical trials, and providing the clinical investigators with tools to make better clinical assessments.

The local database repository 104 may include a clinical trial database 104a, patient profile database 104b, a patient health data database 104c, and a medical record database 104d. The clinical trial database 104a may include information regarding the various trials registered for management by the system 100. The clinical trial database 104a, for example, may include a listing of the inclusion or exclusion criteria established for each registered clinical trial that determine whether a patient is qualified to enroll in the study. The inclusion or exclusion criteria, for example, may involve the weight, age, gender, and/or ethnicity of a patient, the type and stage of a disease that the patient has, previous or current medications that the patient is on, or preexisting medical conditions of the patient. The patient profile database 104b may include basic information regarding clinical trial patients (e.g., age, weight, gender, ethnicity, etc.) along with genomic and metabolic profiles (or any other profile) for the patients. The patient health data database 104c may store real-time health data of clinical trial patients 109 that may be obtained by the system 100 while remotely monitoring the patients 109. The medical record database 104d may include information regarding a patient's medical history including electronic health records (EHRs) and notes entered by clinical investigators 119 through the CTMP interface when conducting a clinical trial. Third party database servers 150 may also provide an external database repository 154 which may include medical knowledge databases 154a that provide a medical knowledgebase upon which the system may draw.

The telemetry devices 110 for clinical trial patients 109 may allow the system 100 to remotely monitor health attributes of a patient. The telemetry device 110 may include a display 118, one or more input/output interfaces 111 (e.g., a keypad, capacitive touch screen, or the like), one or more communication interfaces 113 (e.g., cellular communication interface 113a, wireless communication interface 113b, Bluetooth communication interface 113c, or NFC communication interface 113d), one or more analog or digital sensors 114, and processing circuitry 115, which may include one or more processors 116 and memory 117. The memory 117 may include logic for capturing measurements made by the sensors 114 and relaying the measurements to the system 100 in a continuous, real-time or near real-time, manner.

The sensors 114 of the telemetry device 110 may capture various health attributes (e.g., vital signs) of the patient in a continuous, real-time or near real-time, manner. The telemetry device 110 may be able to process measurements made by the sensors 114 and communicate these measurements to the system 100 in a continuous, real-time or near real-time, fashion. For example, readings or measurements from the sensors 114 may be sent to the system 100 as they are being measured (i.e., in real-time) or at periodic intervals (e.g., every 20 minutes). In some cases, the sensors 114 may be integrated within the telemetry device 110. For example, as illustrated in FIG. 1, the telemetry device 110 may take the form of a smart watch or other wearable device, which may include integrated sensors 114 that measure the heart rate, blood pressure, body temperature and respiratory rate of a patient. In other instances, the sensors 114 may be in communication with the telemetry device 110 (e.g., over the wireless communication interface 113b, Bluetooth communication interface 113c or NFC communication interface 113d), which may then relay the measurements to the system 100. In some therapeutic contexts, for example, the patient 109 may be monitored using an implanted, or in-vivo, diagnostic device, for example, a blood glucose monitor that continuously monitors the blood sugar levels of the patient 109. The ZephyrLIFE HOME platform serves as an example of a commercially available remote patient monitoring (RPM) device, which may act as a communication platform between various sensors 114 that are monitoring the patient attributes and the system 100. As noted above, the system 100 may capture and store the health data received from the telemetry device 110 in the patient health data database 104c in local database repository 104. The system 100 may be configured so as to facilitate the integration of different devices in a seamless manner, thereby allowing the system 100 to be compatible with any device currently available or developed in the future.

The terminals and work stations 120 may allow clinical supervisors 118 and clinical investigators 119 to interact with the system 100 through a CTMP interface. The CTMP interface may present the clinical investigator 119 with a dashboard through which the clinical investigator 119 may, for example and without limitation, register new clinical trials, manage recruitment of patients to the different clinical trials, monitor the health of patients enrolled in the different clinical trials, and assist clinical investigators in making more critical clinical decisions.

Figure 2:
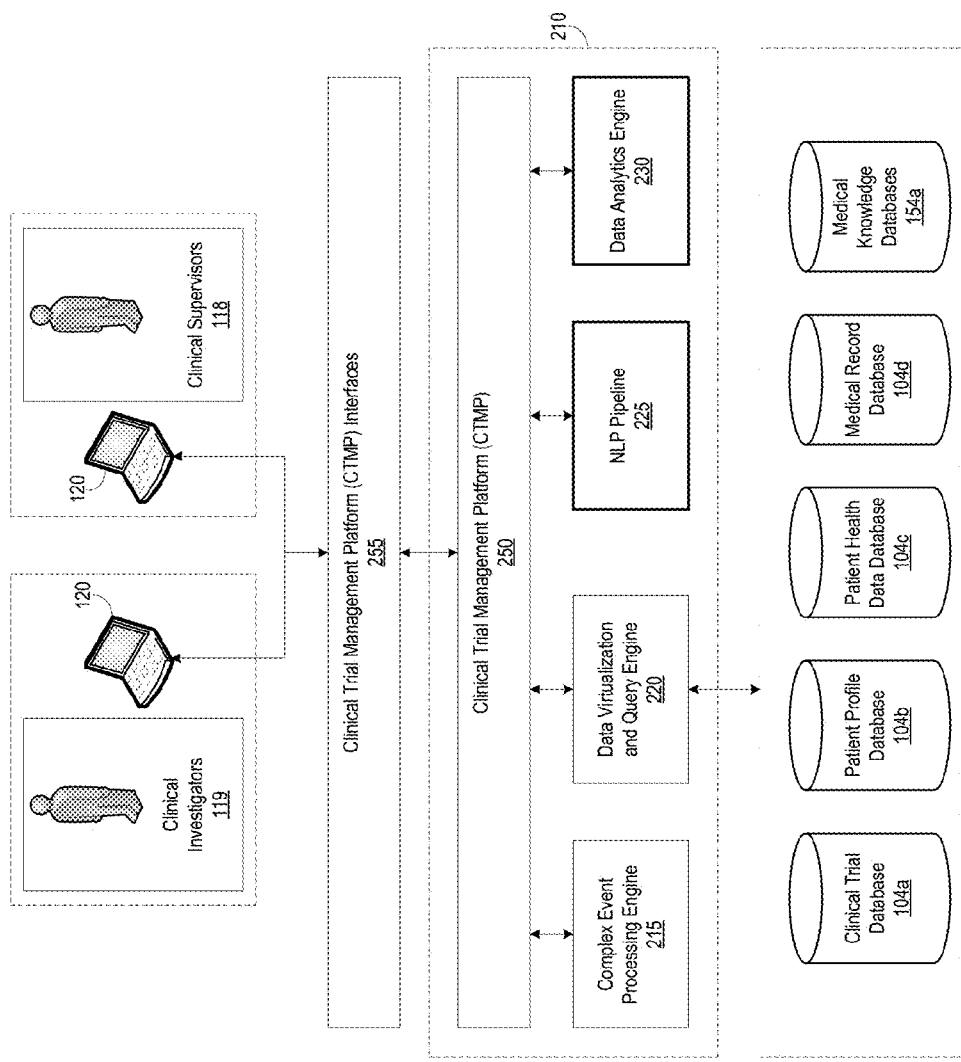
FIG. 2 provides an example of the system architecture on which the clinical trial management system may be implemented.

FIG. 2 provides an example of the system architecture on which the clinical trial management system may be implemented, which may include a server stack 210, operating on the one or more processors 110 of the system 100, which provides the Clinical Trial Management Platform (CTMP) 250. The clinical supervisors 118 and clinical investigators 119 may interact with the CTMP 250 through one or more CTMP interfaces 255. The server stack 210 may include a complex event processing (CEP) engine 215, a data virtualization and query engine 220, a natural language processing (NLP) pipeline 225, and a data analytics engine 230.

The system 100 may utilize the data analytics engine 230 to allow for data exploration, provide data analytics including predictive analytics, and assist with data visualization. The system 100 may use the data analytics engine 230 to process information in the patient profile database 104b, patient health data database 104c, medical record database 104d, and medical knowledge databases 154a and provide the analytics functionality described below. The data analytics engine 230 may rely on natural language processing and machine learning to reveal insights within this information. The data analytics engine 230, for example, may implement analytics to identify medical predispositions, observe and identify relationships within health data and potential adverse events, determine patient specific predictive outcomes and perform a trade-off analysis to identify an optimal course of treatment. The data analytics engine 230 may generate different analytical models that look at the frequency, correlation and deviation between different parameters to identify meaningful patterns within the data, and may provide a score and confidence value for the pattern that is identified. The parameters may be identified by the analytics engine 230 in an automated fashion and/or with the assistance of clinical investigators 119. The data analytics engine 230, for instance, may implement clustering analytics using k-means or latent Dirichlet allocation (LDA) techniques to generate models that group different sets of information having certain common parameters. These models, and other analytics models, may provide a score and confidence value for the different patterns or groupings that are observed. The data analytics engine 230 may also support the dynamic generation of infographics that may help clinical investigators 119 to visualize the data processed by the data analytics engine 230 as well as the relationships identified therein. IBM Watson Analytics is an example of a commercially available solution that provides for the above-described functionality of the data analytics engine 230.

The CEP engine 215 may receive and process patient health data received from telemetry devices 110 in a continuous, real-time, or near real-time, manner. The processing of patient health data may be implemented using computing frameworks (e.g., Apache Spark, an open-source framework) that support stream processing for the CEP engine 215 (e.g., through the Spark Streaming module). Patient health data may be delivered using a data stream that supports queueing. For instance, Kafka streams may be used to deliver patient health data to the CEP engine 250, where the Spark Streaming module may be used to process these incoming Kafka streams. The system 100 may use the computing framework and stream processing modules (e.g., Spark and Spark Streaming) of the CEP engine 250 to process incoming health data.

The system 100 may interface with a plurality of databases through the data virtualization and query engine 220 of the server stack 210, which may allow the system 100 to access data from multiple heterogeneous data sources. The databases may include databases in the local database repository 104 and/or external database repository 154. Given the large amount of data contained in the various databases, the data virtualization and query engine 220 may provide for rapid, model-driven, definition, integration, management and testing of data services. As an example, the server stack 210 may implement a data virtualization and query engine 220 as a Teiid data virtualization and query engine, which is an open source system and part of the JBoss Community of projects. Where the databases share a common database model (e.g., a relational database), the data virtualization and query engine 230 may not be needed. However, where the different databases exist in different forms (e.g., relational databases, hierarchical databases, XML documents, flat files, or the like), the system 100 may utilize the data virtualization and query engine 220.

The system 100 may implement various natural language processing (NLP) methodologies in an NLP pipeline 225. As an example, the NLP pipeline 225 may take the form of the Apache clinical Text Analysis and Knowledge Extraction System (cTAKES), or it may take the form of a generic dependency parser (like ClearNLP), or any other commercial natural language parsers, which are generally available and can be built upon Apache's Unstructured Information Management Architecture (UIMA), which is also available as an open-source product. The system 100 may utilize the NLP pipeline 225 of the server stack 210 to analyze patient medical histories (or other medical text) to identify and capture medical information and relationships in the clinical text.

Generating Patient Specific Genomic Profiles

Since the efficacy of a drug or medical treatment may vary and depend, to a certain degree, on the genetic make-up of a person, pharmacogenomic insights may be helpful in predicting who will respond well to a certain drug or who may experience serious side effects when participating in a clinical drug trial. For example, the presence of an SNP, or combination of SNPs, may indicate whether a patient is at risk for experiencing an adverse event. Similarly, metabolic expression levels may provide an indication of patient risk.

In operation, the system 100 may generate patient specific profiles (e.g., genomic profiles and metabolomics profiles) by analyzing one or more biological samples (e.g., sputum samples) provided by the patient. In some embodiments, the sample may undergo microarray analysis (e.g., an SNP array analysis) to generate a genomic profile that identifies the presence or absence (i.e., a binary indication) of certain SNPs of interest. The SNPs of interest may be selected for testing and inclusion in the genomic profile based on the therapeutic area of the clinical trial in which the patient is enrolled. For example, where the clinical trial is for the treatment of cancer, the microarray analysis may look to identify the presence or absence of rs396991, rs1801131, and rs4149056, which are SNPs having an association with breast cancer and colorectal cancer. The Genome-Wide Human SNP Array 6.0, available from Affymetrix, is an example of a commercially available microarray analysis product that is able to detect over 906,600 different SNPs. In other embodiments, the sample may undergo microarray analysis to generate a SNP profile that provides the presence or absence of biomarkers of interest. The SNP biomarkers of interest may be selected for testing and inclusion in the genomic profile based on the therapeutic area of the clinical trial in which the patient is enrolled. For example, where the clinical trial is for the treatment of cancer, the microarray analysis may look to at the presence of rs396991, rs1801131, and rs4149056. The GeneChip® Human Genome U133 Plus 2.0 Array, available from Affymetrix, is an example of a commercially available microarray analysis product that includes a comprehensive whole human genome expression array covering over 47,000 transcripts. In selecting the SNPs, the system 100 may reference one or more medical knowledge databases 154a (e.g., the PharmGKB database) that indicate whether the SNP, gene or biomarker is associated with a particular disease or therapeutic area, or implicated by a particular drug treatment. The system 100 may capture and store the output of the microarray analysis in the patient profile database 104 using various tools including the commercially available GeneSpring analytical tool from Agilent Technologies.

Patient Tagging and Stratification

As noted above, clinical investigators may be able to improve the success rate of a clinical study by screening patients for a clinical trial or anticipating the need for additional support where serious adverse events are expected based on their genomic and metabolomic profile. By way of example, in a clinical trial for treatment of a type of cancer (e.g., breast cancer) with a particular drug (e.g., Bevacizumab), the presence of a particular SNP or combination of SNPs (e.g., rs1801131) in a patient may indicate that the patient is likely to respond favorably to treatment or that the patient is likely to suffer an adverse event if given the treatment. It may be desirable to include patients that are likely to respond favorably to treatment within the study, while excluding those patients that might respond poorly to treatment.

When a patient profile is generated, the system 100 may tag or otherwise identify a medical predisposition of the patient 110 indicated by the profile of the patient. The medical predisposition may represent the likelihood, or quantified risk, that a particular patient may respond in a particular way to a specific drug treatment (e.g., the risk that a particular patient may suffer an adverse event if given a particular drug treatment) given their particular profile (i.e., based on the SNPs, genes or biomarkers that they exhibit).

The system 100 may identify a genetic predisposition of the patient 110 in different ways. For example, where the genomic profile of the patient identifies different SNPs, the system 100 may identify a genetic predisposition by comparing a type of SNP in the genomic profile of the patient 110 to a known linkage between SNPs, drug type and/or type of adverse events. The SNPs of interest for a clinical trial may be defined in the system 100, for example, by the clinical investigator 119 or based on information in medical knowledge databases 154a, and may be used to place the patient in different risk categories. As another example, the system 100 may interface with medical knowledge databases 154a (e.g., PharmGKB), using the database management and query engine 220, to retrieve known relationships or associations between the genomic profile of the patient and a particular therapy or therapeutic area. The medical knowledge databases 154a, for example, may indicate an association between an SNP and a particular disease and/or drug treatment. As a more specific example, the medical knowledge databases 154a may associate the SNP rs1801131 with breast cancer and favorable treatment by the drug Bevacizumab.

While this association may provide some indication as to the medical predisposition of a patient having the SNP rs1801131, the mechanisms by which an individual patient responds to a particular drug treatment may be quite complex and this complexity may not be captured by the association of a single SNP to a particular drug treatment. For instance, while a patient having the SNP rs1801131 may generally respond favorably to treatment using Bevacizumab, a patient having the SNPs rs1801131 and rs1801133 may not respond well to such a treatment or may even experience an adverse event. The system 100 may be able to better assess these more complex relationships by applying clustering analytics across broader patient populations (e.g., across the clinical trial or the entire patient database) or across a particular subset of a broader patient population (e.g., those patients known to respond positively to a particular drug therapy or therapeutic area).

The system 100 may apply clustering analytics to the patient profiles (e.g., genomic profiles and metabolic profiles) in the patient profile database 104b. The system 100, for instance, may determine that patients having a specific combination of one or more SNPs, genes and/or biomarkers respond favorably to a particular drug treatment, while patients having a different combination of SNPs, genes and/or biomarkers do not. The system 100 may also take into account patient health data stored in patient health database 104c and medical records stored in medical record database 104d when performing the clustering analytics. The system 100, for example, may observe that patients having a particular combination of SNPs experience a particular response (e.g., elevated heart rate or blood pressure) when a particular drug treatment is given. The system 100 may combine the known associations provided by medical knowledge databases 154a with the results of the clustering analytics applied to the patient profiles and patient health data to reach a particular conclusion regarding a predisposition of the patient.

While clinical recruitment typically relies on inclusion and exclusion criteria to identify patients for enrollment in a clinical trial, such methods are not sufficiently robust to identify an ideal set of candidates. As a result patients enrolled in a clinical study may experience serious adverse events, ultimately resulting in the failure of the clinical trial (e.g., for lack of sufficient efficacy and safety data). The system 100 may provide for improved clinical requirement by screening patients based on their tagged medical predispositions. For instance, by identifying patients within a patient population (e.g., those patients meeting the inclusion criteria for the clinical trial) that may be best suited for the clinical trial (i.e., patients that may respond favorably to treatment or patients who are unlikely to experience adverse events), the clinical trial may be more likely to achieve success.

The system 100 may also be able to model the patient recruitment process, which may assist clinical investigators 119 in designing a clinical trial. The system 100, for example, may model the patient recruitment process as a Poisson-Gamma distribution in which patients are enrolled in the trial according to independent Poisson processes, defined by a non-constant parameter λ, which represents the rate of recruitment (i.e., the number of patients recruited per period of time) and indicates how fast recruiting may take place. The system 100 may also be able to model the patient recruitment process at the design stage of the clinical trial (i.e., before the clinical trial has begun) and at various intermediate stages of the clinical trial (i.e., as the trial progresses). Using such a model, the system 100 may be able to predict how long it will take to enroll a sufficient number of suitable patients, which may be an important parameter in designing a clinical trial, or how many patients may be recruited in a particular region, which may affect the power of statistical tests and the amount of drug supply required to satisfy patient demand in different regions.

Real-Time Health Monitoring

As mentioned earlier, the clinical trial process relies on site visits to assess the health and progress of patients enrolled in the trial. Such methods, however, are insufficient to properly track the health of patients enrolled in the trial, particularly where the patient experiences a serious adverse event that requires immediate medical attention. The system 100 may allow clinical investigators 119 to monitor the health of patients remotely so that they may more readily address adverse events experienced by the patient and provide more individualized therapies. As noted above, the patient telemetry devices 110 may provide measurements of health attributes of a patient (e.g., patient vital signs) to the system 100 in a continuous, real-time, or near real-time, manner. The system 100 may be able to process the incoming health data, as it is received, to identify different events experienced by the patient 109, which may be related to the therapy or treatment that the patient 110 is receiving. This may allow clinical investigators 119 to more readily recognize significant events (e.g., positive outcomes or adverse events) and take action when intervention is necessary.

The system 100, for example, may compare health attributes of a patient measured prior to and immediately following administration of a drug treatment or therapy, and may calculate a relative change in the attributes (e.g., as a percentage or in absolute terms) as measured before and after administration of the drug. In this way, the system 100 may be able to determine the relative impact that a particular drug treatment has on a patient attribute that is being observed, and may help to establish a causal relationship between the two (i.e., between the drug treatment and the patient's physiological response). For example, in a clinical trial for heart disease, the system 100 may observe a decrease in a patient's blood pressure following administration of an increased dosage of a particular drug and may conclude that the treatment was effective in treating heart disease. The system 100 may apply different rules, which may be defined by the clinical investigators 119 or based on information in medical knowledge databases 154*a*, to identify significant responses, and may generate a score, or confidence value, in the relationship that is identified.

The system 100 may also leverage the patient profiles (e.g., genomic profile and patient profile) to validate the observed relationship. The system 100, for example, may analyze the patient profiles (e.g., using the above-described clustering analysis techniques) to determine whether such a response was expected, and may adjust the confidence value accordingly. Continuing with the previous example, the system 100 may analyze the genomic profile of the patient to determine whether the patient's genomic profile indicated that the patient's blood pressure would decrease after taking the particular drug. If the genomic profile provided such an indication (i.e., included a specific combination of SNPs, genes or biomarkers), the system 100 may increase the confidence value associated with the identified relationship. Conversely, if the genomic profile suggested that the patient would not respond to the drug treatment or that the patient's blood pressure would increase in response to the drug treatment, the system 100 may decrease the confidence value. The system 100 may present the identified relationship, confidence value and patient profiles to the clinical investigator 119 through the CTMP interface for validation.

The system 100 may also apply different rules to determine whether an adverse event has been experienced by the patient. The system 100, for example, may compare incoming patient data to a baseline value or historical average of the patient 109, which may be defined in the system 100, for example, by the clinical investigator 119 or based on information in medical knowledge databases 154*a*. For instance, if the incoming patient data (e.g., patient heart rate) exceeds the baseline value by a certain amount (e.g., more than 35% above a baseline value or historical average), and/or for a certain period of time, the system 100 may determine that the patient is potentially experiencing an adverse event. The system 100 may generate a score, or confidence value, regarding whether the observed response is an adverse event. The system 100 may also leverage the patient profiles (e.g., genomic profile and patient profile) to determine validate the adverse event determination, and may adjust the confidence value accordingly. The system 100, for example, may analyze the patient profiles (e.g., using the above-described clustering analysis techniques) to determine whether such a response was expected, and may adjust the confidence value accordingly.

The system 100 may also generate an alert directing the clinical investigator 119 to verify the determination and investigate whether the patient is, in fact, experiencing an adverse event. The alert may be communicated to the clinical investigator over any number of communication channels including, for example, SMS messaging and/or e-mail. The alert generated by the system 100 may provide general information regarding the observed patient response (e.g., patient id and health attribute values) and contain a link (e.g., a hyperlink) directing the clinical investigator 119 to a Uniform Consolidated Output (UCO) provided through the CTMP interface, where the clinical investigator 119 may be able to investigate the situation further.

The system 100 may also track each alert to determine whether the clinical investigator 119 has reviewed the alert and taken any necessary action. The system 100, for example, may determine whether the link was activated (i.e., clicked or otherwise selected) by the clinical investigator 119, or whether the clinical investigator 119 marked the alert as being addressed in the CTMP interface. The system 100 may also implement an escalation system in order to ensure that patients receive the appropriate level of attention. The system 100, for example, may associate an escalation flag with an alert when the alert is generated (e.g., an initial value of 1). If the clinical investigator 119 attends to the alert within a specified period of time (e.g., within two hours), the escalation flag may be reset (e.g., set to 0) and the alert may be cleared. If the alert is not attended to within certain periods of time, the escalation flag may be increased (e.g., to 2, 3, 4, etc.). The system 100 may trigger notification of a clinical supervisor if the escalation flag reaches a specified value (e.g., a value of 5). In some instances, for example, where the alert is deemed to be critical importance (e.g., where a heart attack is detected), the escalation flag may immediately trigger notification of the clinical supervisor (e.g., the initial value may be set to 5).

The system 100 may also provide the clinical investigators 119 with predictive tools that the clinical investigator 119 may use to assess the risk or likelihood of a patient experiencing a particular physiological response (e.g., an adverse event) and/or develop personalized drug regimes. The system 100, for example, may be able to process historical patient health data, medical records, and notes previously recorded by clinical investigators 119 (e.g., using machine learning techniques) to develop a personalized model for a particular patient, which may predict how the patient may respond if given a particular drug treatment. The system 100, for instance, may be trained using data of a patient population or subpopulation (e.g., data of patients enrolled in the trial or patients who have already undergone treatment), and based on the current health attributes of a patient (e.g., a patient who has yet to undergo treatment), may be able to predict the value of health attributes or the outcome that is expected if a particular drug treatment is given. By way of example, the system 100 may observe that a patient undergoing treatment for a particular disease experienced an adverse event (e.g., increase in blood pressure) when the drug dosage (e.g., increased by 2 mg) and/or root of administration (e.g., intravenous) was changed. By analyzing health data of several patients, the system 100 may be able to model the likelihood of different potential outcomes, allowing the clinical investigator 119 to determine how best to proceed. The system 100 may also apply tradeoff analytics to the model that is generated by the system 100 to help clinical investigators 119 make decisions regarding the type of treatment that a particular patient is given. The tradeoff analytics, for example, may suggest an optimal drug treatment (e.g., a particular type and dosage quantity) or different drug treatment options having different predicted outcomes (e.g., an aggressive treatment option or a conservative treatment option that may have different risks and likelihood of success) based on the model that is generated.

Clinical Trial Management Platform (CTMP) Interface

As noted above, the system 100 may provide clinical investigators 119 with a CTMP interface through which the clinical investigators 119 may register new clinical trials, manage recruitment of patients to the different clinical trials, monitor the health of patients enrolled in the different clinical trials, and assist clinical investigators in making more critical clinical decisions.

As it relates to managing recruitment of patients to the different clinical trials, the CTMP interface may provide clinical investigators 119 with a clinical recruitment tool, which may help the clinical investigator 119 identify patients to enroll in a clinical trial by filtering the patient population, for example, based on inclusion and exclusion criteria. The CTMP interface may additionally, or alternatively, filter the patient population based on the patient profiles (e.g., genomic and metabolomic profiles) and associated medical predisposition tags, which may be identified by applying the clustering analytic techniques described above. The clinical recruitment tool, for example, may identify groupings of patients who are likely to respond favorably to the particular drug treatment, groupings of patients who likely to respond poorly to a particular drug treatment or groupings of patients who may be at risk for experience adverse events. The clinical recruitment tool may also provide a confidence value associated with the various groupings. The clinical investigator 119 may be able to act accordingly, for example, by enrolling some patients in the clinical trial or by planning to provide additional care to trial participants 109 that may be inclined or predisposed to experience any adverse event.

With regard to monitoring the health of patients enrolled in the different clinical trials and assisting clinical investigators in making clinical decisions, the CTMP interface may provide the clinical investigator 119 with an adverse event alert tool to investigate and respond to adverse events that are identified by the system 100. The adverse event alert tool, for example, may present the clinical investigator 119 with a listing of adverse events, which may identify patients that are potentially experiencing adverse events (e.g., by patient ID) and provide general information regarding the patient and the adverse event (e.g., basic demographic information and the current health attributes of the patient). The clinical investigator 119 may be able to select one or more adverse event alerts to investigate further, for example, those of a particular patient or those of a group of patients exhibiting similar behavior. In response, the clinical investigator 119 may be presented with a Uniform Consolidated Output (UCO) that provides a consolidated view of the health data, medical history, and genomic profile (along with any other relevant patient profiles) of the patient (or patients).

The UCO may provide a summary that illustrates the presence of different SNPs. The UCO may also provide the clinical investigator 119 with clinical insights derived by the system 100. As discussed previously, for example, the system 100 may analyze the patient profiles (e.g., genomic profile) to determine whether an adverse event was expected for the patient. The UCO may also include a section where a clinical investigator 119 may provide notes or other observations for a specific patient that may be gathered during a patient visit. The system 100 may leverage these "notes" when performing analytics, for example, text analytics for natural language classification. The UCO may present this analysis to the clinical investigator 119 and indicate the confidence value of the determination, for example, in the graph or chart of the patient profile.

As noted above, the system 100 may process real-time health data to determine the relative impact that a particular drug treatment has on a patient attribute that is being observed, and may help to establish a causal relationship between the two. The UCO may allow the clinical investigator 119 to investigate and verify the observed relationship, for example, by allowing the clinical investigator 119 to visualize the measured physiological reaction of the patient 109 and the patient profile associated with the same patient 109. The UCO may also allow the clinical investigator 119 to look at the medical predisposition data in a broader context, for example, providing the investigator 119 with (or allowing the investigator to explore) predisposition data of different patient populations (e.g., all patients associated with a particular clinical testing site).

The UCO may also provide predictive tools that may allow the clinical investigator 119 to suggest how treatment for that patient should proceed. The system 100, for example, may identify similar patients (i.e., other patients having similar genomic or metabolomics profiles) that have undergone the same or similar treatment experienced by the patient thus far, and may analyze subsequent treatment outcomes to determine the most effective medication or most efficacious dosage.

Figure 3:
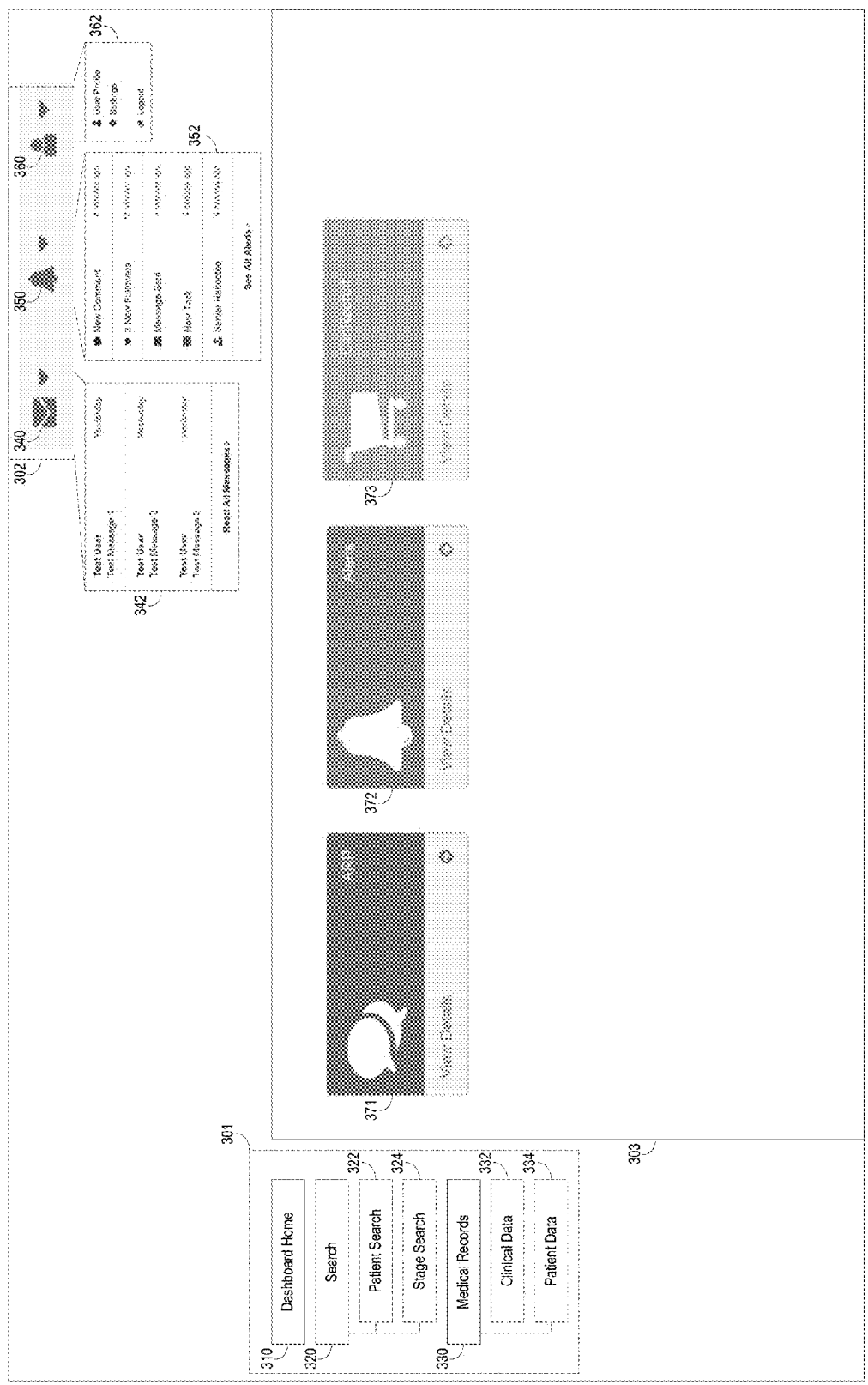
FIG. 3 illustrates an example of a first view provided through an interface that the system may provide to clinical investigators.

FIG. 3 illustrates an example of a dashboard view provided through the CTMP interface provided to clinical investigators. The interface may include a first toolbar 301, a second toolbar 302 and a viewing pane 303. The first and second toolbars 301, 302 may be similarly presented throughout the different interface views, while the viewing pane 303 may present different information in the different interface views.

The first toolbar 301 may include a dashboard home button 310, a search button 320, and a medical records button 330 and the second toolbar 302 may include a user message button 340, a user alerts button 350, and a user profile button 360. The dashboard home button 310, when selected by a clinical investigator 119, may direct the interface to present the dashboard view illustrated in FIG. 3. The search button 320, when selected by a clinical investigator 119, may cause two additional buttons, a patient search button 322 and stage search button 324, to be displayed. The patient search button 322 and stage search button 324, when selected by a clinical investigator 119, may present the inventor with corresponding search views. The medical records button 330, when selected by a clinical investigator 119, may cause two additional buttons, a clinical data button 332 and a patient data button 334, to be displayed. The clinical data button 332, when selected by a clinical investigator 119, may present the clinical investigator 119 with an interface through which the clinical investigator 119 may browse clinical data, for example, data stored in medical knowledge databases 154a. The patient data button 334, when selected by a clinical investigator 119, may present the clinical investigator 119 with an interface through which the clinical investigator 119 may visualize patient health data, which may be gathered in real time, stored in patient health data database 104c or patient medical records (e.g., EHRs) stored in medical record database 104d.

As for the second toolbar 302, the user message button 340, when selected by a clinical investigator 119, may present a drop-down menu 342 to the clinical investigator 119 listing messages recently received by the clinical investigator 119. The user alerts button 350, when selected by a clinical investigator 119, may present a drop-down menu 352 to the clinical investigator 119 listing different alerts received by the clinical investigator 119. As illustrated in FIG. 3, these alerts may include new comment notifications, social media notifications, messaging notifications, task notifications and server information notifications. The user profile button 360, when selected by a clinical investigator 119, may present a drop-down menu 362 to the clinical investigator 119, through which the clinical investigator 119 may view their profile, adjust the interface settings, or logout of the interface.

In the dashboard view, the viewing pane 303 may provide one more links, including links to an ARP tool 371, an adverse event alert tool 372, and a clinical recruitment tool 373. The clinical recruitment tool 373 may allow the clinical investigator 119 to design and register new clinical trials, enroll patients in planned or ongoing trials, and manage the patient recruitment process. The adverse event alert tool 372, when selected by a clinical investigator 119, may present the clinical investigator 119 with a list of different alerts for the clinical investigator to explore. As discussed above, an alert may be provided to the clinical investigator 119 in situations where patient vital signs (or other monitored health attribute) have exceeded a threshold value. Through the tool, the clinical investigator 119 may be able to drill down on specific alerts, for example, those of a particular patients or those of a group of patients exhibiting similar behavior (i.e., elevated blood pressure levels). When drilling down into a specific alert, the clinical investigator 119 may be provided with a Uniform Consolidated Output (UCO).

Figure 4:
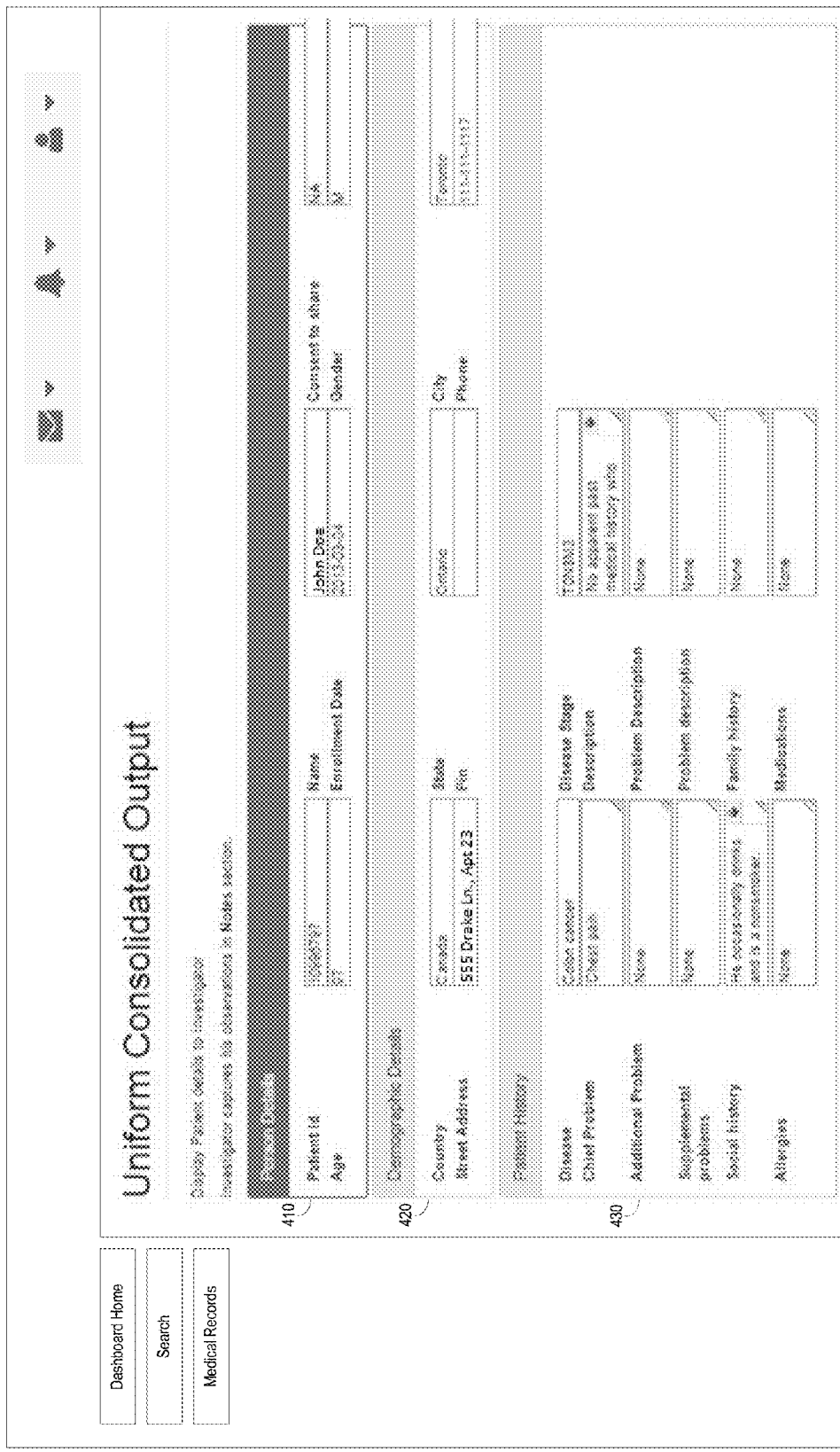
FIG. 4 illustrates an example of a first view of a uniform consolidated output provided through an interface that the system may provide to clinical investigators.
Figure 5:
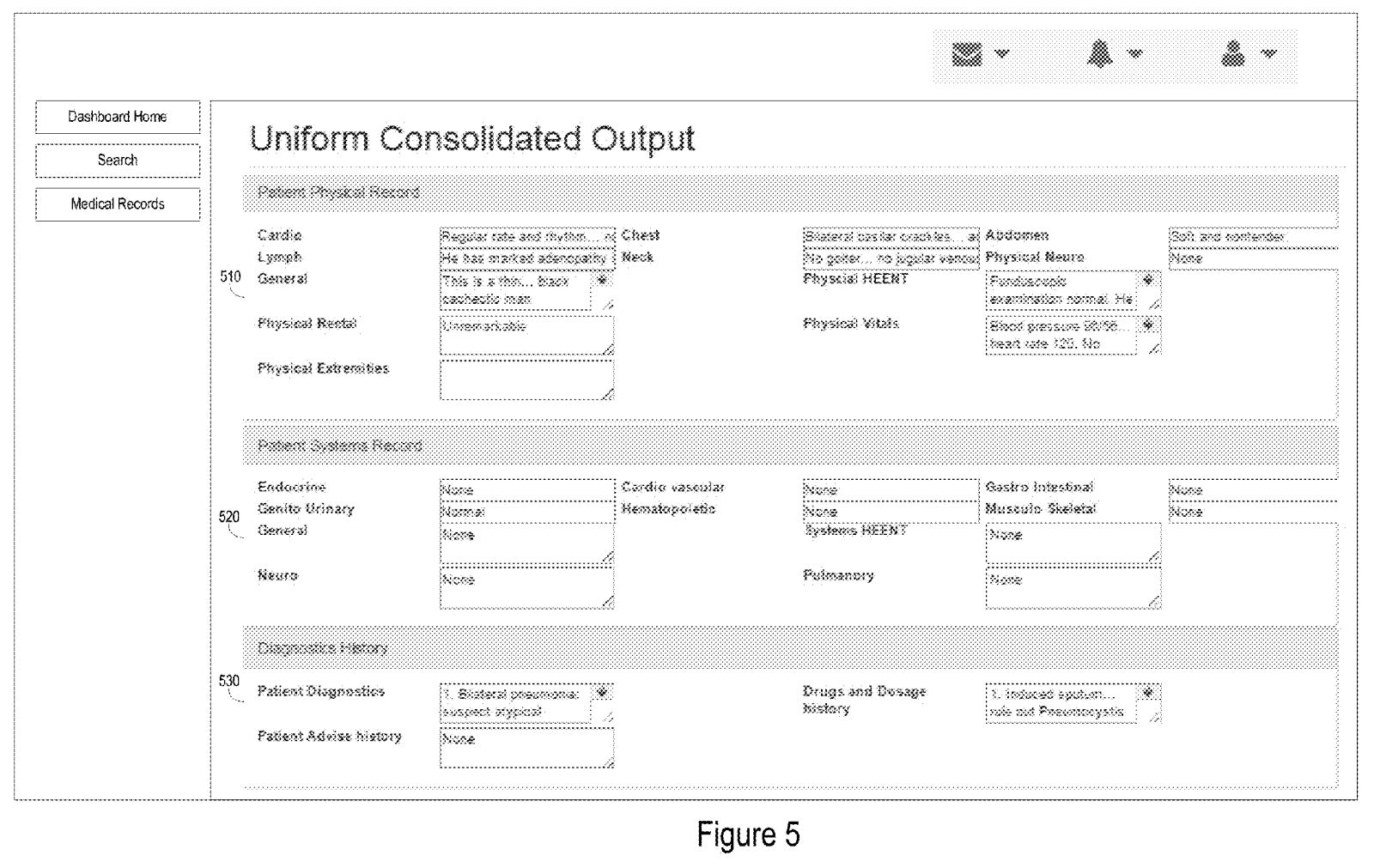
Figure 6:
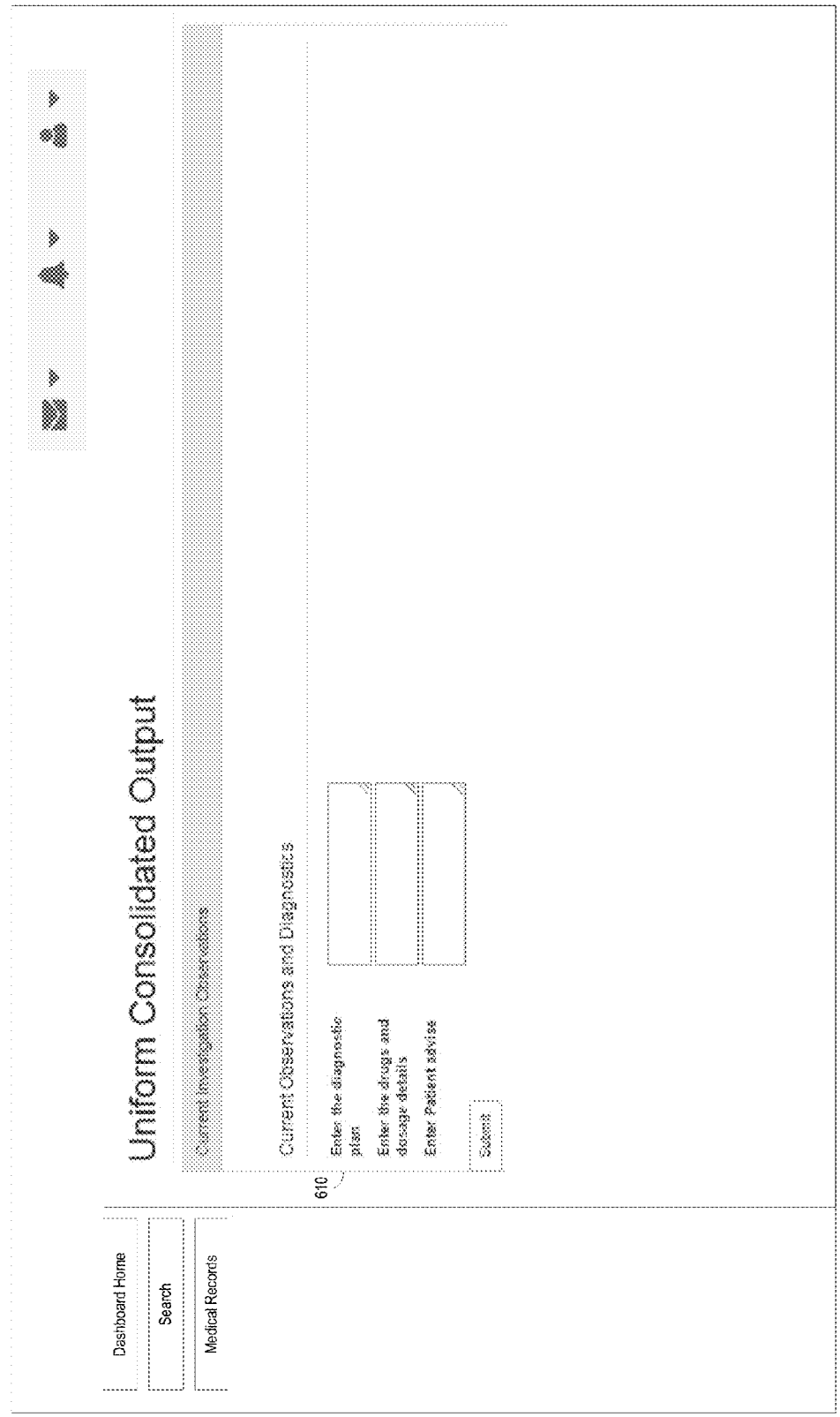
FIG. 6 illustrates an example of a third view of a uniform consolidated output provided through an interface that the system may provide to clinical investigators.

FIGS. 4-7 illustrate an example of different views of a UCO provided for a clinical patient through the CTMP interface that the system 100 may provide to clinical investigators 119. The clinical investigator 119 may be able to scroll between the different views when interacting with the interface. As illustrated in FIG. 4, the UCO may provide personal details 410 regarding the patient, demographic details of the patient 420, and a summary of the patients medical history 430. With reference to FIG. 5, the UCO may include a summary of patient physical records 510, patient systems records 520, and diagnostics history 530. The UCO, as shown in FIG. 6, may also provide an observation entry form 610 through which clinical investigator 119 may enter notes regarding the patient and the drug treatment that they are receiving, which the system 100 may store (e.g., in medical record database 104d) and process, as described above. The system 100, for instance, may apply natural language processing techniques to analyze the data provided in the observation notes. By way of example, the system may identify the presence or frequency of the word "tachycardia" or the phrase "increased heart rate" and determine that the patient (or similar patients) may be at risk of a shoot up in heart rate when an associated drug treatment is administered.

Figure 7:
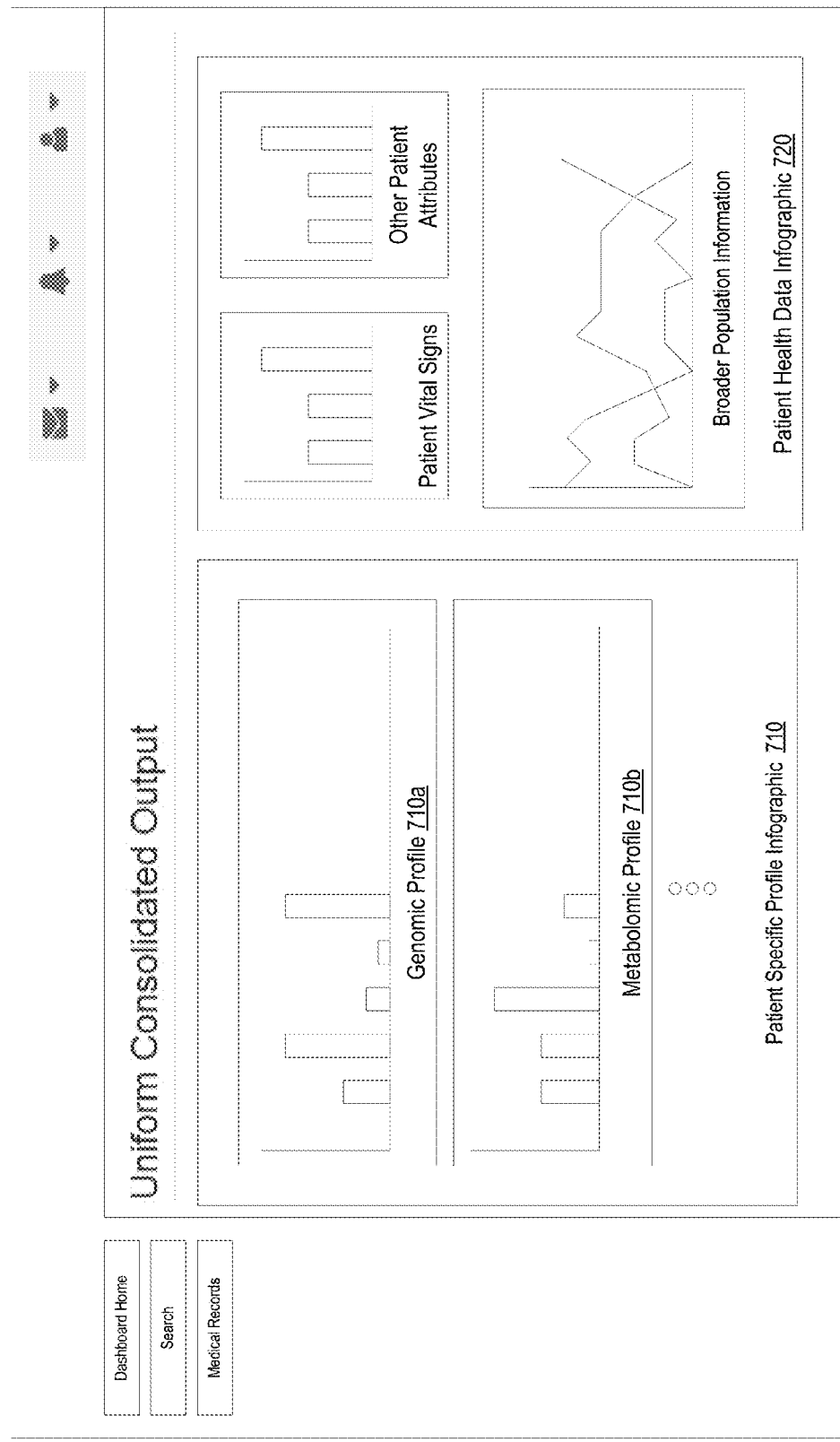
FIG. 7 illustrates an example of a fourth view of a uniform consolidated output provided through an interface that the system may provide to clinical investigators.

FIG. 7 illustrates an example of an additional view of the UCO provided through the CTMP interface. The UCO may provide a patient profile infographic 710 depicting the different patient profiles (e.g., genomic profile 710a and/or metabolomic profile 710b. The UCO may also provide a patient health data infographic 720 depicting the different patient health attributes (e.g., patient vital signs or other health attributes) being monitored by the system 100. The patient health data infographic 720 may present the values for the health attributes that are being monitored in real-time, as well as a comparison against the patients historical average, a baseline value, and/or a broader patient population (e.g., patients with the clinical trial or patients exhibiting a similar drug response). By providing the patient profiles, patient health data, and patient medical records through the UCO, the clinical investigator 119 may be able to visualize or otherwise identify relationships or adverse events between a measured physiological reaction of the patient and a particular drug treatment. The UCO may also present some of the deeper analytics described above (e.g., predictive analytics) to the clinical investigator 119. The UCO, for example, may present the medical predispositions identified by the system 100 (e.g., in the form of a visual indicator), and may additionally allow the clinical investigator 119 to look at patient profiles in a broader context, for example, providing the investigator 119 with (or allowing the investigator to explore) predisposition data of different patient populations (e.g., all patients associated with a particular clinical testing site). The UCO may also allow the clinical investigator to visualize different patient-specific outcomes that may be expected if a particular drug treatment is administered.

Figure 8:
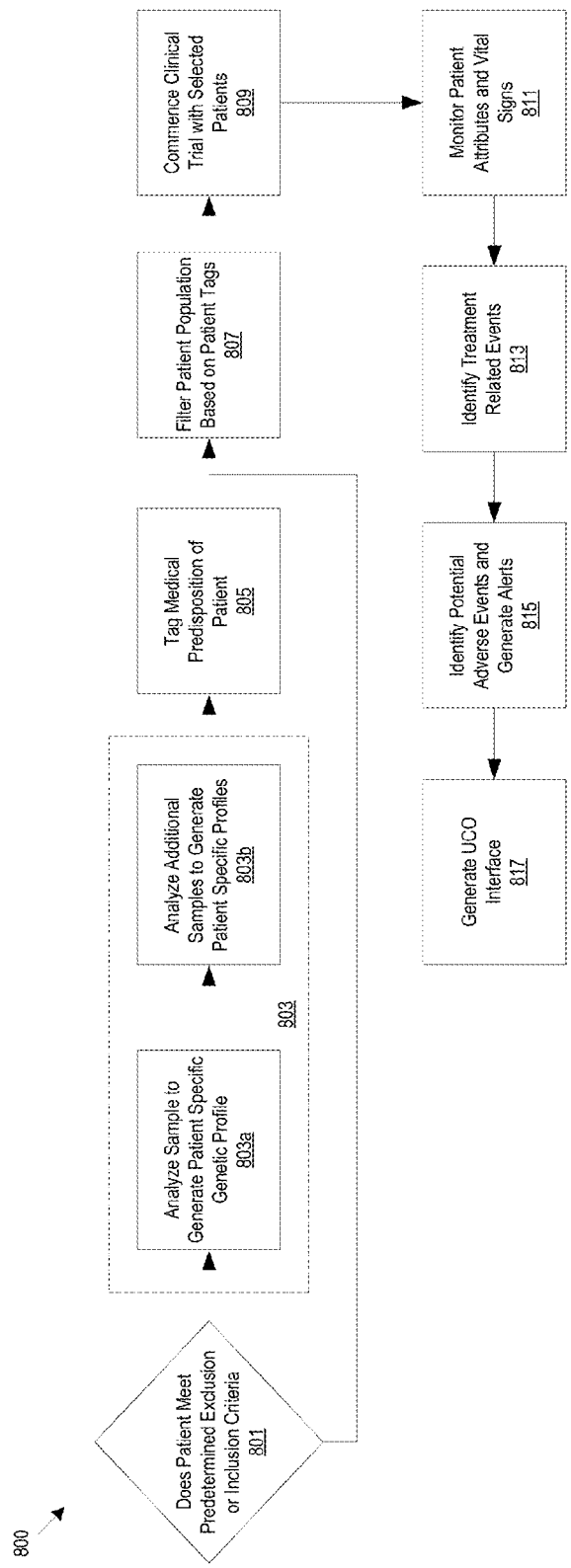
FIG. 8 illustrates one embodiment of the logic that the system may employ in providing telemetric patient monitoring to support clinical trial management.

FIG. 8 illustrates one embodiment of the logic that the system 100 may employ in providing telemetric patient monitoring to support clinical trial management. A patient 109 may volunteer for a clinical trial for a particular drug or medical treatment, and may undergo testing to see if certain predetermined criteria for inclusion or exclusion from the study are met (801). If the patient 109 satisfies the requirements, the patient may be able to enroll in the clinical trial. Next, the system 100 may generate one or more patient profiles (e.g., genomic profiles and metabolomics profiles) by analyzing one or more biological samples (e.g., sputum samples) provided by the patient 109 (803). The system 100, for example, may perform microarray analysis (e.g., an SNP array analysis) on a biological sample provided by the patient 109 to generate a genomic profile for the patient (803a). The genomic profile may identify the presence or absence of certain SNPs, where the SNPs of interest may be selected for testing and inclusion in the genomic profile based on the therapeutic area of the clinical trial in which the patient is enrolled. The system may also analyze additional samples provided by the patient 109 to determine transcriptomic, proteomic, metabolomic, and autoantibody profiles for the volunteer, which may also be stored in the patient profile database 104b (803b). The system 100, having determined one or more profiles, may proceed to tag or otherwise identify a medical predisposition of the patient 109 and may rely on clustering analytics to do so (805). This process may repeat until numerous different patients 109 have enrolled in the clinical trial. The system 100 may then filter the patient population for the clinical trial based on the medical predispositions that have been identified in order to identify patients that may be best suited for the clinical trial, and determine what additional measures, if any, may be necessary to address potential adverse events (807).

Once the clinical investigator 119 has selected the appropriate patients 109 to enroll in the clinical trial, the trial may commence and the drug treatments may begin (809). The system 100 may remotely monitor one or more health attributes of the enrolled patients including, for example, the heart rate, blood pressure, body temperature and respiratory rate of the patients, which may be provided to the system 100 by patient telemetry devices 110 (811). In some contexts, the patient monitoring may be continuous, but in others the monitoring may only take place for a certain interval of time surrounding the administration of a drug treatment (i.e., before and after a dose is given). The system 100 may store the patient health data in patient health data database 104c. The system 100 may also process the patient data as it is received from the telemetry devices 110 to identify different physiological events experienced by the patient 109, which may be related to the therapy or treatment that the patient 109 is receiving (813). The system 100 may also compare the patient data to a baseline value (e.g., a pre-dose baseline, a steady state dose baseline, a patient population or subpopulation average, or the like) to identify potentially adverse events experienced by the patients 109, and may generate an alert, which may be brought to the attention of clinical investigators 119 (815). The system 100 may generate a CTMP interface, which may provide the clinical investigator 119 with tools to investigate and respond to adverse events that are identified by the system 100. The CTMP interface may present the clinical investigator 119 with a consolidated view that displays the health data, medical history, and genomic profile (along with any other relevant patient profiles) of the patients (817).

In one embodiment, the system may build a patient profile database for one or more SNPs, where the one or more genes are selected based on a therapy or a therapeutic area associated with the clinical trial. Building the patient profile database may involve determining whether a patient meets certain predetermined clinical trial inclusion criteria or exclusion criteria, and when the patient meets the criteria enrolling the patient in the clinical trial, obtaining a patient sample for analysis, analyzing the patient sample, by obtaining the presence or absences of SNPs associated with the trial, to generate a patient specific genetic profile, and storing the genetic profile in a database and associating the genetic profile with the patient and each of the one or more genes. The system may also build a patient metabolic expression database for one or more metabotypes, where the one or more metabotypes are selected based on a therapy or a therapeutic area associated with the clinical trial, where the patient metabolic expression database includes patient specific metabolic profiles that include a metabolic expression level for each of the one or more metabotypes.

The system may further tag the patient for a genetic predisposition, for each of the one or more genes, based on the patient specific genetic profile, or tag the patient for a metabolic predisposition, for each of the one or more metabotypes, based on the patient specific metabolic profile. Tagging the patient for a genetic predisposition may involve defining the presence or absence for the one or more SNPs, (e.g., by performing a microarray analysis), and identifying a genetic predisposition of the patient based on the presence or absence of an SNP marker to form a genetic predisposition table. Tagging the patient for a metabolic predisposition may involve defining a baseline metabolic expression level for the one or more genes, determining an exhibited metabolic expression level for the patient for the one or more metabotypes, assigning a metabolic status indicator to the exhibited metabolic expression level based on a comparison of the exhibited metabolic expression level to the baseline metabolic expression level, and identifying a metabolic predisposition of the patient based on the metabolic status indicator assigned to the exhibited metabolic expression level to form a metabolic predisposition table.

The system may also monitor one or more patient attributes, including patient vital signs such as a heartbeat rate, a blood pressure, a body temperature, and a respiration rate, to identify a medical event occurrence, where the one or more patient attributes are related to the therapy or therapeutic area associated with the clinical trial. Monitoring the patient attributes may involve obtaining data indicative of the one or more patient attributes from one or more medical devices or sensors, determining a relative change in the one or more patient attributes, where the relative change is assessed at different points of time, defining a baseline attribute level for each of the one or more patient attributes, assigning a status indicator to the one or more patient attributes based on a comparison of the relative change in the one or more patient attributes to the baseline attribute level, and generating an alert based on the status indicator assigned to the one or more patient attributes.

The system may also generate an interface that provides a representation of the patient specific genetic profile and patient specific metabolic profile, a representation of the one or more patient attributes, and a representation of broader population information, and identifies statistically significant relationships between the patient specific genetic profile and/or patient specific metabolic profile and the medical event experienced by the patient.

In another embodiment, the system may obtain a patient sample for analysis from a prospective patient, analyze the patient sample to generate a prospective patient genetic profile, where analyzing the patient sample involves determining the presence or absence of a particular SNP sequence, retrieve one or more patient specific genetic profiles from the SNP database, where the patient specific genetic profiles include an indication of the presence or absence of the SNP sequence and identify a genetic predisposition of the patient. The system may additionally compare the prospective patient genetic profile to the one or more patient specific profiles to determine a potential genetic predisposition of the prospective patient, and make a suitability determination of whether the prospective patient is suitable for a clinical trial The methods, devices, processing, and logic described above may be implemented in many different ways and in many different combinations of hardware and software. In some embodiments, dedicated hardware implementations, including application specific integrated circuits, programmable logic arrays and other hardware devices, can be constructed to implement one or more of the methods described herein. One or more embodiments described herein may implement functions using two or more specific interconnected hardware modules or devices with related control and data signals that can be communicated between and through the modules, or as portions of an application-specific integrated circuit. For example, all or parts of the implementations may be circuitry that includes an instruction processor, such as a Central Processing Unit (CPU), microcontroller, or a microprocessor; an Application Specific Integrated Circuit (ASIC), Programmable Logic Device (PLD), or Field Programmable Gate Array (FPGA); or circuitry that includes discrete logic or other circuit components, including analog circuit components, digital circuit components or both; or any combination thereof. The circuitry may include discrete interconnected hardware components and/or may be combined on a single integrated circuit die, distributed among multiple integrated circuit dies, or implemented in a Multiple Chip Module (MCM) of multiple integrated circuit dies in a common package, as examples.

The circuitry may further include or access instructions for execution by the circuitry. The instructions may be stored in a tangible storage medium that is other than a transitory signal, such as a flash memory, a Random Access Memory (RAM), a Read Only Memory (ROM), an Erasable Programmable Read Only Memory (EPROM); or on a magnetic or optical disc, such as a Compact Disc Read Only Memory (CDROM), Hard Disk Drive (HDD), or other magnetic or optical disk; or in or on another machine-readable medium. A product, such as a computer program product, may include a storage medium and instructions stored in or on the medium, and the instructions when executed by the circuitry in a device may cause the device to implement any of the processing described above or illustrated in the drawings.

The implementations may be distributed as circuitry among multiple system components, such as among multiple processors and memories, optionally including multiple distributed processing systems. Parameters, databases, and other data structures may be separately stored and managed, may be incorporated into a single memory or database, may be logically and physically organized in many different ways, and may be implemented in many different ways, including as data structures such as linked lists, hash tables, arrays, records, objects, or implicit storage mechanisms. Programs may be parts (e.g., subroutines) of a single program, separate programs, distributed across several memories and processors, or implemented in many different ways, such as in a library, such as a shared library (e.g., a Dynamic Link Library (DLL)). The DLL, for example, may store instructions that perform any of the processing described above or illustrated in the drawings, when executed by the circuitry.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A method comprising:
building, by a processor of a server, a profile database comprising subject profiles of one or more subject traits for one or more subjects;
analyzing, by the processor, the subject profiles in the profile database and tagging a subject profile for the one or more subjects with a response predisposition based on the analysis, the response predisposition representing a likelihood that an individual subject will have a particular response to a specific treatment;
enrolling, by the processor, the one or more subjects in a trial and storing corresponding enrollment indications in a trial management database;
monitoring, with a telemetric device in communication with the server, one or more physiological attributes of the one or more subjects enrolled in the trial to identify an event occurrence, the monitoring comprising,
receiving, by the processor, data indicative of the one or more physiological attributes from the telemetric device,
defining, by the processor, a baseline level for each of the one or more physiological attributes,
determining, by the processor, a relative change for each of the one or more physiological attributes based on data obtained at different points in time;
identifying, by the processor, an event occurrence based on a determination that the relative change has exceeded the baseline level for at least one of the physiological attributes, and
validating, by the processor, the event occurrence based on the subject profiles;
generating, by the processor, an event alert based on an identification of the event occurrence;
generating, by the processor, an interactive interface for the event alert providing a representation of the subject profile for a subject associated with the event alert and a representation of the one or more physiological attributes for the subject associated with the event alert;
including, by the processor, a link in the event alert for the interactive interface that is generated; and
transmitting, by the processor, the event alert over a communication channel to a remote device for a trial investigator.

2. The method of claim 1, wherein building the profile database further comprises:
obtaining a biological sample of a subject for analysis;
analyzing the biological sample for the one or more subject traits and generating a subject specific profile based on the analysis; and
storing the subject specific profile in the profile database and associating the subject specific profile with a subject identification number and each of the one or more subject traits.

3. The method of claim 1, wherein tagging the one or more subjects comprises, for each individual subject of the one or more subjects, performing clustering analytics on the subject profiles to identify a combination of subject traits indicative of the response predisposition.

4. The method of claim 3, wherein performing the clustering analytics also accounts for subject attribute data, subject history data, and known response predispositions.

5. The method of claim 1, wherein enrolling the one or more subjects comprises, for each individual subject of the one or more subjects:
determining whether the individual subject matches criteria for the trial defined in the trial management database;
determining whether the individual subject has been tagged with response predispositions associated with the trial;
filtering out the individual subject based on a determination that the response predisposition is unfavorable; and
enrolling the individual subject based on a determination that the response predisposition is favorable.

6. The method of claim 1, further comprising:
tracking the event alert to determine whether the event alert has been reviewed and whether any action was taken; and
escalating the event alert based on a determination that the alert has not been reviewed or a determination that no action was taken.

7. The method of claim 2, wherein the analyzing the biological sample comprises performing a microarray analysis on the biological sample and generating a subject specific genomic profile based on the analysis.

8. The method of claim 1, wherein the one or more physiological attributes are vital signs, including one or more of a heart beat rate, a blood pressure, a body temperature, and a respiration rate.

9. A system comprising:
a processor and a memory in communication with the processor, the processor configured to:
build a profile database comprising subject profiles of one or more subject traits for one or more subjects;
analyze the subject profiles in the profile database and tag a subject profile for the one or more subjects with a response predisposition based on the analysis, the response predisposition representing a likelihood that an individual subject will have a particular response to a specific treatment;
enroll the one or more subjects in a trial and store corresponding enrollment indications in a trial management database;
receive, from a telemetric device configured to monitor one or more physiological attributes of the one or more subjects enrolled in the trial, data indicative of one or more physiological attributes from the telemetric device;
define a baseline level for each of the one or more physiological attributes;
determine a relative change for each of the one or more physiological attributes based on data obtained at different points in time;
identify an event occurrence based on a determination that the relative change has exceeded the baseline level for at least one of the physiological attributes;
generate, in response to the determination that the relative change has exceeded the baseline level for at least one of the physiological attributes, an interactive interface providing a representation of the subject profile for a subject associated with the event occurrence and a representation of the one or more physiological attributes for the subject associated with the event occurrence;
generate an event alert based on an identification of the event occurrence, the event including a link in the event alert for the interactive interface that is generated; and
transmit the event alert to a trial investigator over a communication channel.

10. The system of claim 9, wherein in building the profile database the processor is configured to:
obtain a biological sample of a subject for analysis;
analyze the biological sample for the one or more subject traits and generate a subject specific profile based on the analysis; and
store the subject specific profile in the profile database and associating the subject specific profile with a subject identification number and each of the one or more subject traits.

11. The system of claim 9, wherein in tagging the one or more subjects, the processor, for each individual subject of the one or more subjects, is configured to:
perform clustering analytics on the subject profiles to identify a combination of subject traits indicative of the response predisposition.

12. The system of claim 11, wherein the processor is configured to perform clustering analytics that also account for subject attribute data, subject history data, and known response predispositions.

13. The system of claim 9, wherein in enrolling the one or more subjects, the processor, for each individual subject of the one or more subjects, is configured to:
determine whether the individual subject matches criteria for the trial defined in a criteria database;
determine whether the individual subject has been tagged with response predispositions associated with the trial;
filter out the individual subject based on a determination that the response predisposition is unfavorable; and
enroll the individual subject based on a determination that the response predisposition is favorable.

14. The system of claim 9, wherein the processor is further configured to:
track the event alert to determine whether the event alert has been reviewed and whether any action was taken; and
escalate the event alert based on a determination that the alert has not been reviewed or a determination that no action was taken.

15. The system of claim 10, wherein in analyzing the biological sample, the processor is configured to:
perform a microarray analysis on the biological sample and generate a subject specific genomic profile based on the analysis.

16. The system of claim 9, wherein the one or more physiological attributes are vital signs, including one or more of a heart beat rate, a blood pressure, a body temperature, and a respiration rate.

17. The system of claim 9, wherein the processor is further configured to:
determine, by the processor, based the analysis of the subject profiles, a confidence value that the event occurrence corresponds to the particular response to the specific treatment; and
include an indication of the confidence value in the interactive interface.

* * * * *